(12) United States Patent
Wu

(10) Patent No.: US 9,664,583 B2
(45) Date of Patent: May 30, 2017

(54) DEVICE FOR CALIBRATING A TORQUE WRENCH

(71) Applicant: Matatakitoyo Tool Co., Ltd., Taichung (TW)

(72) Inventor: Yi Min Wu, Taichung (TW)

(73) Assignee: MATATAKITOYO TOOL CO., LTD., Taichung (TW)

( * ) Notice: Subject to any disclaimer, the term of this patent is extended or adjusted under 35 U.S.C. 154(b) by 201 days.

(21) Appl. No.: 14/530,788

(22) Filed: Nov. 2, 2014

(65) Prior Publication Data
US 2016/0123832 A1    May 5, 2016

(51) Int. Cl.
| A61C 1/00 | (2006.01) |
| G01L 25/00 | (2006.01) |
| A61C 1/18 | (2006.01) |
| B25B 23/142 | (2006.01) |
| A61C 8/00 | (2006.01) |

(52) U.S. Cl.
CPC ............ *G01L 25/003* (2013.01); *A61C 1/186* (2013.01); *A61C 8/0001* (2013.01); *B25B 23/1427* (2013.01); *G01L 25/00* (2013.01)

(58) Field of Classification Search
CPC .................................................. G01L 25/003
USPC ......................................................... 73/1.12
See application file for complete search history.

(56) References Cited

U.S. PATENT DOCUMENTS

| D244,829 | S | * | 6/1977 | Lehoczky ........................ D8/24 |
| 4,125,016 | A | * | 11/1978 | Lehoczky ........... B25B 23/1425 |
| | | | | 73/862.23 |
| 4,517,821 | A | * | 5/1985 | Taggart ................. G01L 25/003 |
| | | | | 702/113 |
| D281,854 | S | * | 12/1985 | Grabovac ..................... D10/122 |
| D282,815 | S | * | 3/1986 | Grabovac ....................... D10/83 |
| D286,973 | S | * | 12/1986 | Grabovac ........................ D8/24 |
| 4,761,989 | A | * | 8/1988 | McDevitt ............. H02K 49/106 |
| | | | | 310/103 |
| 5,571,014 | A | * | 11/1996 | Gregory, Jr. ......... A61C 8/0089 |
| | | | | 433/126 |
| 6,119,562 | A | * | 9/2000 | Jenkins ............... B25B 23/1425 |
| | | | | 81/479 |
| 6,167,788 | B1 | * | 1/2001 | Schonberger ........... B25B 23/14 |
| | | | | 73/862.23 |
| 6,234,051 | B1 | * | 5/2001 | Bareggi .............. B25B 23/0035 |
| | | | | 73/862.21 |

(Continued)

FOREIGN PATENT DOCUMENTS

EP        3018463      *   5/2016   ............. G01L 25/00

OTHER PUBLICATIONS

ASI Datamyte, Inc., Residual Torque Analyser, WO2009039497, Mar. 26, 2009, pp. 1-29.*

(Continued)

*Primary Examiner* — Clayton E Laballe
*Assistant Examiner* — Kevin Butler

(57) ABSTRACT

A device for calibrating a torque wrench includes a base plate, a strain gauge, a display, a cup, a rod and a ring. The strain gauge is non-rotationally connected to the base plate. The display is electrically connected to the strain gauge. The cup is non-rotationally connected to the base plate. The rod is non-rotationally connected to the cup. The ring is inserted in the cup so that the ring and the cup together define an annular gap for tightly receiving a socket.

10 Claims, 5 Drawing Sheets

(56) References Cited

U.S. PATENT DOCUMENTS

| | | | | |
|---|---|---|---|---|
| D520,309 S * | 5/2006 | Hsien | | D8/25 |
| D533,038 S * | 12/2006 | Hsu | | D8/24 |
| D562,093 S * | 2/2008 | Wu | | D8/24 |
| D575,604 S * | 8/2008 | Vossbrinck | | D8/24 |
| D580,720 S * | 11/2008 | Shiao | | D8/24 |
| D623,491 S * | 9/2010 | Vossbrinck | | D8/24 |
| D687,688 S * | 8/2013 | Hsieh | | D8/24 |
| D688,106 S * | 8/2013 | Lee | | D8/24 |
| D719,801 S * | 12/2014 | Theissen | | D8/24 |
| D743,762 S * | 11/2015 | Theissen | | D8/24 |
| D754,501 S * | 4/2016 | Theissen | | D8/24 |
| 2002/0152849 A1 * | 10/2002 | Jenkins | | B25B 23/1427 81/479 |
| 2008/0271515 A1 * | 11/2008 | Dabrowski | | G01L 25/003 73/1.12 |
| 2010/0107779 A1 * | 5/2010 | Hsieh | | G01L 25/003 73/862.21 |
| 2011/0023576 A1 * | 2/2011 | Mountz | | G01L 5/24 73/1.12 |
| 2012/0031161 A1 * | 2/2012 | Hsieh | | B25B 23/1427 73/1.12 |
| 2012/0055227 A1 * | 3/2012 | Chen | | G01L 25/003 73/1.12 |
| 2012/0055228 A1 * | 3/2012 | Herbold | | G01L 25/003 73/1.12 |
| 2013/0047799 A1 * | 2/2013 | Gareis | | B25B 13/467 81/467 |
| 2014/0165796 A1 * | 6/2014 | Gauthier | | A61B 17/8875 81/479 |
| 2014/0331829 A1 * | 11/2014 | King | | B25B 23/1422 81/467 |
| 2015/0369686 A1 * | 12/2015 | Lawson | | G01L 5/24 73/1.12 |
| 2016/0123832 A1 * | 5/2016 | Wu | | G01L 25/003 73/1.12 |
| 2016/0161354 A1 * | 6/2016 | Jiang | | G01L 25/003 73/1.12 |

OTHER PUBLICATIONS

Examiner Lee, Seung Huwan, International Search Report WO2009039497, Apr. 13, 2009, pp. 1-4.*

Examiner Lee, Seung Huwan, Written Opinion of the International Searching Authority, Apr. 13, 2009, pp. 1-4.*

* cited by examiner

DEVICE FOR CALIBRATING A TORQUE WRENCH

BACKGROUND OF INVENTION

1. Field of Invention

The present invention relates to a torque wrench and, more particularly, to a device for calibrating a torque wrench.

2. Related Prior Art

A mechanical device for calibrating a torque wrench is disclosed in Taiwanese Patent Publication No. 538859. The mechanical device includes a shell 10, an axle 21, a block 23, an elastic bar 24, a positioning element 25 and a meter 40. The axle 21 includes a middle section inserted in the shell 10 and two ends 22 located out of the shell 10. The block 23 is attached to the middle section of the axle 21. The elastic bar 24 includes an upper end inserted in the axle 21 and a lower end in contact with the positioning element 25 located in and attached to the shell 10. The meter 40 includes a probe 42, an indicator 43 and a scale (not numbered). The probe 42 includes a lower end in contact with the block 23 and an upper end connected to the indicator 43. The indicator 43 is rotatable with respect to the scale. In operation, a boxed or open end 51 of a torque wrench 50 is engaged with one of the ends 22 of the axle 21 while the shell 10 is secured to a workbench or held by a user. The axle 21 is rotated by the torque wrench 50. The block 23 is rotated while the elastic bar 24 is deformed. The probe 42 is lifted so that the indicator 43 is rotated relative to the scale. Thus, the torque exerted on the axle 21 is measured by the calibrating device. However, the reading of the torque is affected by the angle of the observation of the indicator 43 relative to the scale. Moreover, there are errors in such a mechanical configuration so that the reading of the torque might not reflect the real value of the torque exerted on the axle 21 by the torque wrench 50.

An electric device for calibrating a torque wrench is disclosed in Taiwanese Patent I341235. The electric device includes a shell 20, a rod 30, an elastic bar 40, a sensor 60 and an electric display unit 70. The rod 30 includes a middle section (not numbered) inserted in the shell 20 and two ends 34 located out of the shell 20. The elastic bar 40 includes an end inserted in the axle 21 and another end in contact with a rotating element 54 attached to a frame 52 located in and attached to the shell 20. The sensor 60 is a strain gauge attached to the elastic bar 40. The electric display unit 70 includes a display 72 electrically connected to the sensor 60. In operation, a boxed or open end of a torque wrench is engaged with one of the ends 34 of the rod 30 while the shell 20 is secured to a workbench or held by a user. One of the ends 34 of the rod 30 is rotated by the torque wrench via the rod 30, which is accordingly rotated. Thus, the elastic bar 40 is deformed. The sensor 60 senses the deformation of the elastic bar 40 and accordingly sends a signal to the electric display unit 70 which accordingly calculates the value of the torque exerted in the rod 30 and shows the value on the display 72. The pivoting of the torque wrench is however not smooth.

Therefore, the present invention is intended to obviate or at least alleviate the problems encountered in prior art.

SUMMARY OF INVENTION

It is the primary objective of the present invention to provide a smooth device for calibrating a torque wrench.

To achieve the foregoing objective, the device includes a base plate, a strain gauge, a display, a cup, a rod and a ring. The strain gauge is non-rotationally connected to the base plate. The display is electrically connected to the strain gauge. The cup is non-rotationally connected to the base plate. The rod is non-rotationally connected to the cup. The ring is inserted in the cup so that the ring and the cup together define an annular gap for tightly receiving a socket.

Other objectives, advantages and features of the present invention will be apparent from the following description referring to the attached drawings.

BRIEF DESCRIPTION OF DRAWINGS

The present invention will be described via detailed illustration of two embodiments referring to the drawings wherein.

DETAILED DESCRIPTION OF EMBODIMENTS

Figure 1:
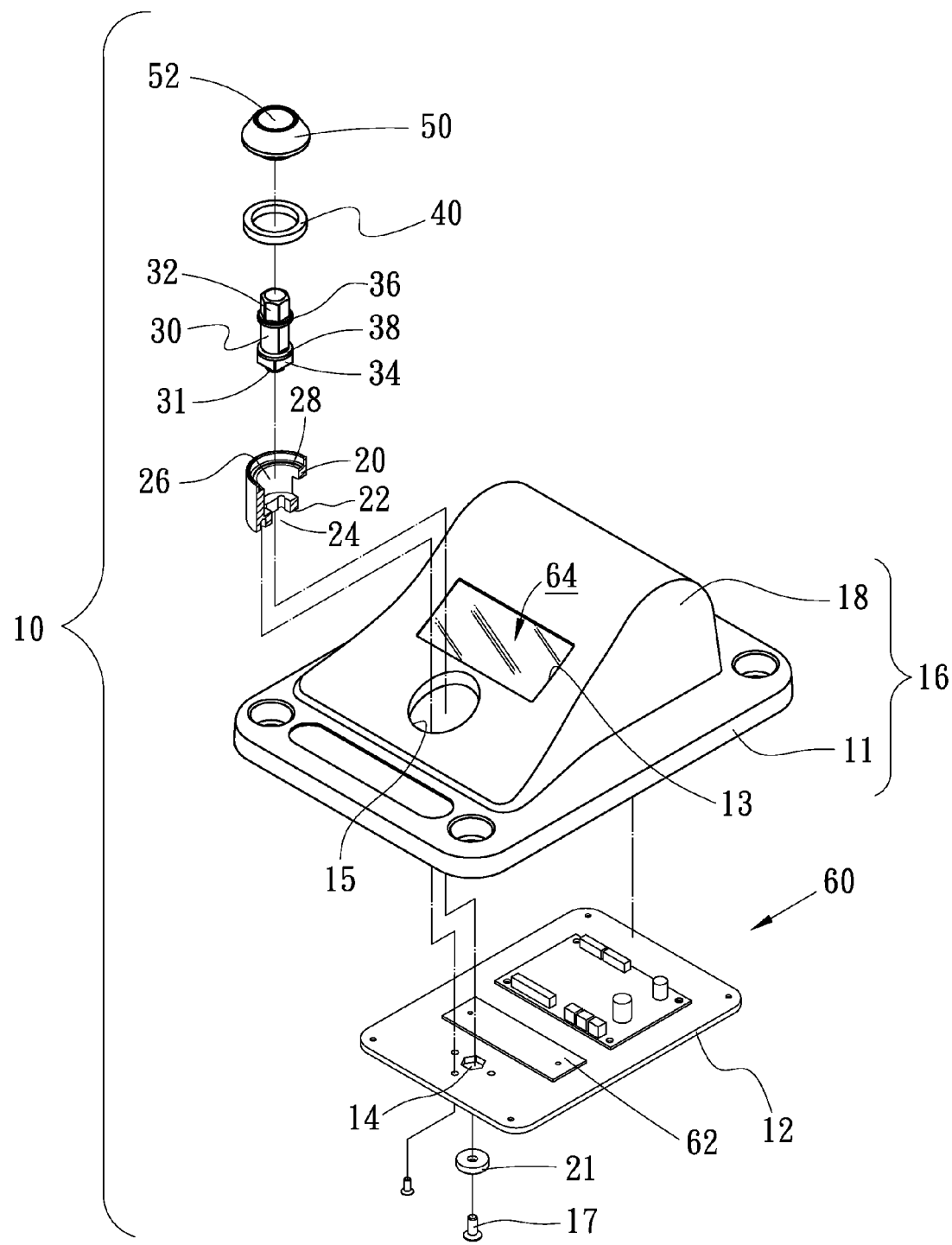
FIG. 1 is an exploded view of a device for calibrating a torque wrench according to the first embodiment of the present invention.
Figure 2:
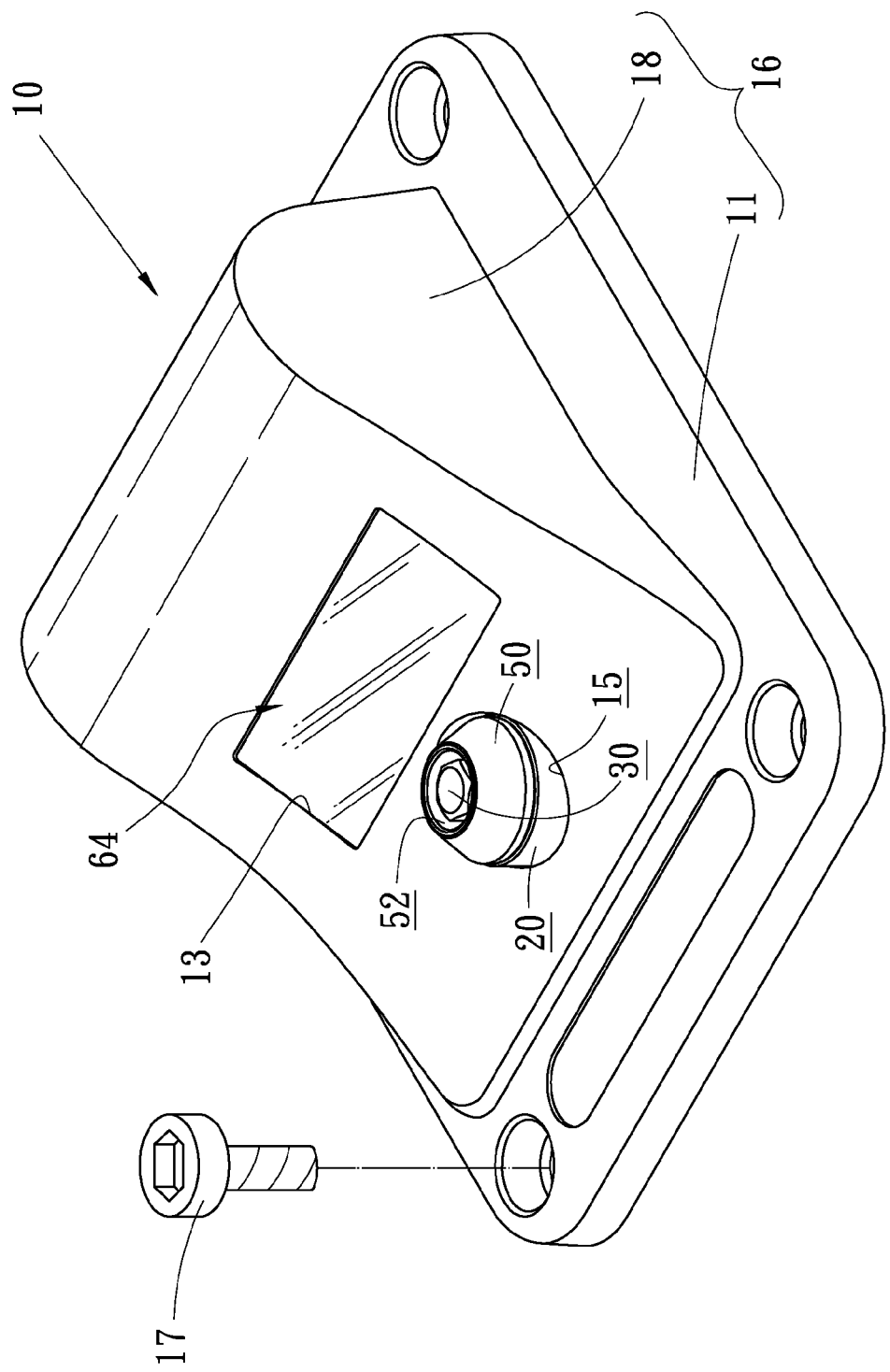
FIG. 2 is a perspective view of the device shown in FIG. 1.
Figure 3:
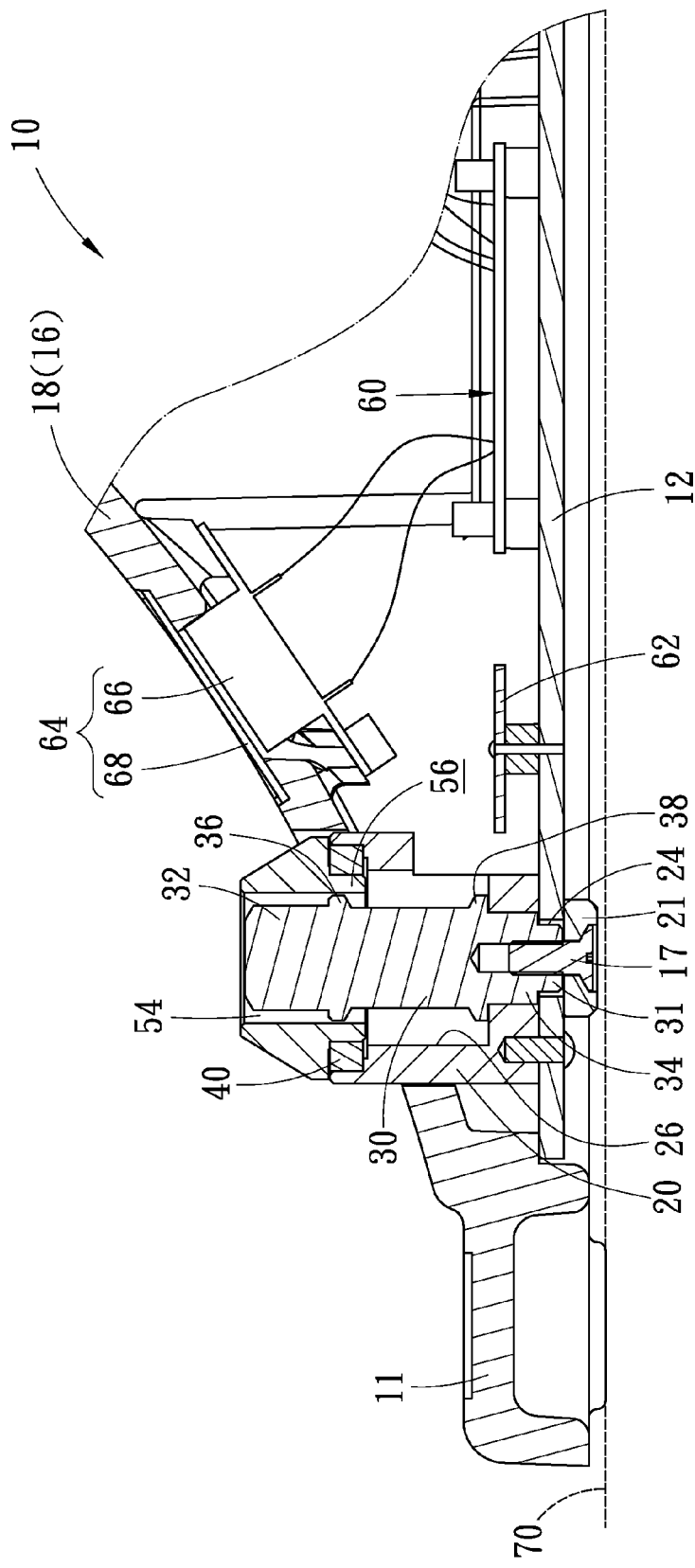
FIG. 3 is a partial, cross-sectional view of the device shown in FIG. 2.
Figure 4:
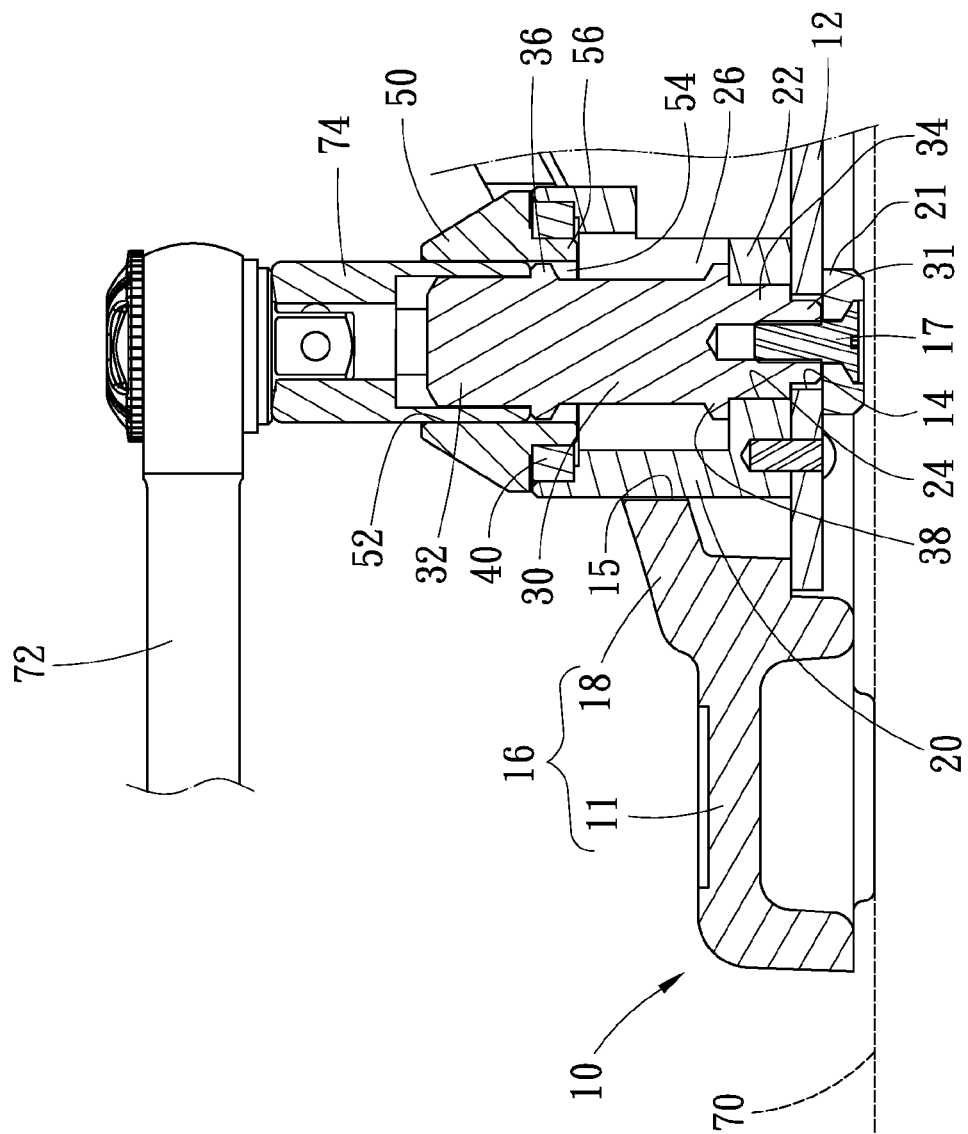
FIG. 4 is a partial, side view of a torque wrench engaged with the device shown in FIG. 3.

Referring to FIGS. 1-4, a device 10 for calibrating a torque wrench includes a base plate 12, a shell 16, a cup 20, a rod 30, a bearing 40, a ring 50 and an electronic unit 60 according to a first embodiment of the present invention. The base plate 12 includes an opening 14.

The shell 16 includes a brim 11 and a crown 18. The brim 11 extends around the crown 18. The crown 18 is made with a window 13 and an opening 15.

The cup 20 includes a lower portion 22. A square opening 24 is made in the lower portion of the cup 20. The cup 20 includes a space 26 in communication with the square opening 24. The space 26 is made of a stepped shape so that an annular shoulder 28 is formed on an internal side of the cup 20.

The rod 30 includes a circular section 31, a square section 34, a lower annular flange 38, an upper annular flange 36 and a hexagonal section 32. The square section 34 is formed on the circular section 31. The lower annular flange 38 is formed on the square section 34. The upper annular flange 36 is formed above the lower annular flange 38. The hexagonal section 32 is formed on the upper annular flange 36.

The bearing 40 can be a ball bearing or a roller bearing.

The ring 50 includes an opening 52 and an annular lip 56. The opening 52 is centrally made in the ring 50. The annular lip 56 extends from a lower side of the ring 50.

The electronic unit 60 includes a circuit board (not numbered), a strain gauge 62 and a display unit 64. The display unit 64 includes a display 66 and a glass panel 68.

The cup 20 is supported on the base plate 12. Three screws (not numbered) are driven in screw holes made in the lower portion 22 of the cup 20 through apertures (not numbered) made in the base plate 12. Thus, the cup 20 is secured to the base plate 12.

The circular section 31 of the rod 30 is inserted in the opening 14 of the base plate 12. A screw 17 is driven in a screw hole (not numbered) made in the circular section 31 of the rod 30 through an aperture made in a washer 21. The aperture of the washer 21 is made of a diameter marginally larger than that of the screw 17. The washer 21 expands larger than the opening 14. Thus, the rod 30 is kept in position. The square section 34 of the rod 30 is inserted in the square opening 24 of the cup 20. The lower annular flange 38 is supported on the lower portion 22 of the cup 20. The upper annular flange 36 is inserted in the space 26 of the cup 20. The hexagonal section 32 of the rod 30 is located out of the space 26 of the cup 20.

The bearing 40 is supported on the annular shoulder 28 of the cup 20. The bearing 40 is flush with the upper annular flange 36.

The annular lip 56 is inserted in and supported on the bearing 40 so that the ring 50 is allowed to smoothly rotate on the bearing 40. The upper annular flange 36 and the hexagonal section 32 of the rod 30 are inserted in the opening 52 so that an annular gap 54 is defined between the rod 30 and the ring 50.

The circuit board and the strain gauge 62 are supported on the base plate 12. The strain gauge 62 is secured to the base plate 12 so that the strain gauge 62 can be deformed with the base plate 12. The strain gauge 62 is electrically connected to the circuit board.

The glass panel 68 is fit in the window 13. The display 66 is attached to the crown 18 so that the display 66 is observable through the window 13. The display 66 is protected by the glass panel 68. The display 66 is electrically connected to the circuit board.

The brim 11 is secured to the base plate 12 by screws (not shown). Thus, the circuit board and the strain gauge 62 are closed by the base plate 12 and the shell 16.

In calibration of a torque wrench 72, a socket 74 connected to the torque wrench 72 is placed on the hexagonal section 32 of the rod 30. A force is exerted on the torque wrench 72 so that a torque is exerted on the socket 74. Hence, the torque is transferred into the rod 30. Then, the torque is transferred to the cup 20. Finally, the torque is transferred to the base plate 12 so that the base plate 12 is deformed, and so is the strain gauge 62. The strain gauge 62 sends a signal corresponding to the deformation. Thus, the value of the torque is calculated and shown on the display 66. The value of the torque shown on the display 66 is compared with a reading of the torque shown on the torque wrench 72. Thus, the torque wrench 72 is calibrated.

Advantageously, the socket 74 is inserted in the annular gap 54. That is, an internal side of the socket 74 is in contact with the hexagonal section 32 of the rod 30 and an external side of the socket 74 is in contact with the ring 50. That is, the socket 74 is guided by both of the rod 30 and the ring 50. The ring 50 is allowed to smooth rotate as it is supported on the bearing 40. Hence, the rotation of the socket 74 is smooth, and so is the pivoting of the torque wrench 72. Moreover, the socket 74 is supported on the upper annular flange 36.

Figure 5:
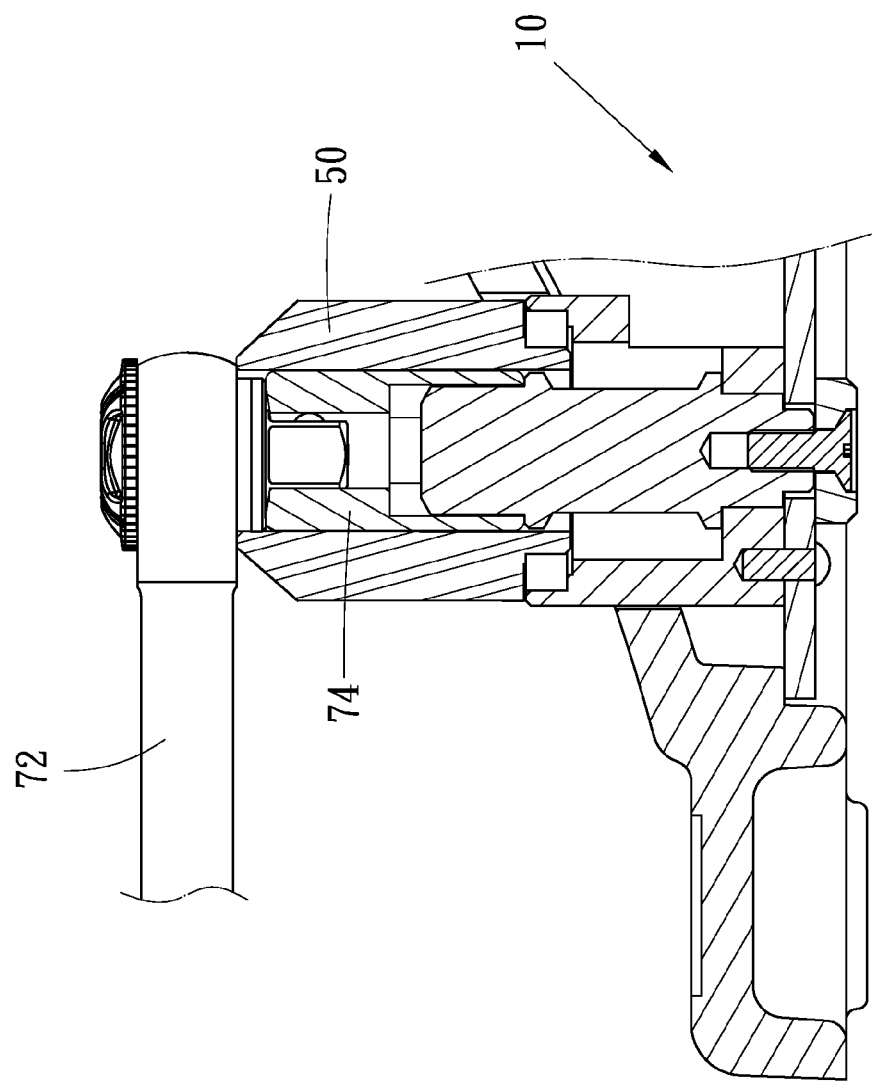
FIG. 5 is a partial, cross-sectional view of a device for calibrating a torque wrench according to the second embodiment of the present invention.

Referring to FIG. 5, there is a device for calibrating a torque wrench according to a second embodiment of the present invention. The second embodiment is identical to the first embodiment except including an axially longer ring 50.

The present invention has been described via the detailed illustration of the embodiments. Those skilled in the art can derive variations from the embodiments without departing from the scope of the present invention. Therefore, the embodiments shall not limit the scope of the present invention defined in the claims.

The invention claimed is:

1. A device for calibrating a torque wrench including:
a base plate;
a strain gauge non-rotationally connected to the base plate;
a display electrically connected to the strain gauge;
a cup non-rotationally connected to the base plate;
a rod non-rotationally connected to the cup;
a ring inserted in the cup so that the ring and the rod together define an annular gap for tightly receiving a socket; and
a bearing placed between the ring and the cup.

2. The device according to claim 1, wherein the ring includes an annular lip inserted in the bearing.

3. The device according to claim 1, wherein the cup includes a lower portion made with a square opening, wherein the rod includes a square section inserted in the square opening of the cup.

4. The device according to claim 3, further including a screw driven in the rod via a washer to keep the rod in position.

5. The device according to claim 3, wherein the rod includes a lower annular flange placed on the lower portion of the cup.

6. The device according to claim 5, wherein the rod includes an upper annular flange for supporting the socket.

7. The device according to claim 1, further including a shell for covering the strain gauge.

8. The device according to claim 7, wherein the shell includes a window for exposing the display.

9. The device according to claim 8, further including a glass panel fit in the window, over the display.

10. The device according to claim 7, wherein the shell includes an opening through which the rod extends.

* * * * *